United States Patent [19]

Wright et al.

[11] Patent Number: 4,870,099

[45] Date of Patent: Sep. 26, 1989

[54] SULFIRCIN AND DERIVATIVES THEREOF AS THERAPEUTIC AGENTS

[75] Inventors: Amy E. Wright; Peter J. McCarthy, both of Ft. Pierce, Fla.

[73] Assignee: Harbor Branch Oceanographic Institution, Inc., Ft. Pierce, Fla.

[21] Appl. No.: 197,349

[22] Filed: May 23, 1988

[51] Int. Cl.$^4$ .................... A61K 31/34; C07D 307/42; C07D 307/46

[52] U.S. Cl. .................................. 514/461; 514/471; 549/497

[58] Field of Search ................. 549/497; 514/461, 471

[56] References Cited

U.S. PATENT DOCUMENTS 4,368,205  1/1983  Engel .................................. 549/497

Primary Examiner—Richard L. Raymond
Attorney, Agent, or Firm—Carroll F. Palmer

[57] ABSTRACT

Novel sesterterpene compounds are derived from marine sponges of the genus Ircinia. These compounds and pharmaceutical compositions containing them as active ingredients are useful in the treatment of fungal infections.

7 Claims, No Drawings

SULFIRCIN AND DERIVATIVES THEREOF AS THERAPEUTIC AGENTS

FIELD OF THE INVENTION

This invention relates to new organic compounds and compositions that have useful therapeutic properties. More particularly, the invention relates to novel sesterterpene compounds derived from marine organisms, i.e., sponges of the genus Ircinia, compositions comprising such compounds and their methods of use for therapeutic and other purposes.

BACKGROUND OF THE INVENTION

Prevention of the growth of fungi and prevention of infections and maladies caused by fungi to mammals and plants has received much attention by scientists and industry since fungi may cause various diseases and infections in man including mycotic disease, e.g., pulmonary candidiasis and pulmonary aspergillosis. Certain yeastlike organisms e.g., *Cryptotococcus neoformans*, may cause serious infections of the central nervous system. More commonly known fungal infections in humans and mammals include ringworm, which are fungal infections of hair and nail areas, as well as resistant infections of the skin. Many other fungal infections inflict humans and other mammals in the areas of skin, mucous membranes, intestinal tract, vaginal area and lungs.

Plants are also attacked by various fungi. Damage caused by fungal infection to agriculture amounts to billions of dollars annually. Various inorganic and organic fungistats and fungicides have been tried, but with limited success. It is, of course, important for the fungicide to kill the fungi, but not the plant and to leave no toxic residue on the food product of the plant.

Various methods have been utilized to combat fungal infection in agriculture, including foliage fungicides wherein plants are coated with a weather-resistant fungicide. Seed treatment and soil treatment methods are also know using fungicides safe for seeds and resistant to degradation by soil or soil borne microorganisms. Chemotherapeutants are fungicides which permeate the plant to protect new growth or eliminate infections which have already occurred within the plant. Agricultural fungistats and fungicides and their application must meet very stringent requirements and regulations that have been promulgated by governmental authorities.

Considerable research and resources have been devoted to combating fungal infections in both mammals and plants. While some antifungal agents and methods have been developed that aid in inhibiting the spread of fungi and fungi caused diseases in both mammals and plants and in treating fungi infected hosts, new methods and antifungal compositions are needed. The present invention concerns the discovery of novel compounds that help to fill such need.

Hence, an object of this invention is the provision of new organic compounds and compositions which have useful therapeutic properties.

Another object is the provision of novel sesterterpene compounds derived from a marine organism, i.e., sponges of the genus *Ircinia aff. I. paucifilamentosa*, new compositions comprising such compounds and their methods of use for antifungal and other purposes.

The full scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The objects of the invention are accomplished, in part, by the provision of novel compounds of the formulae I & II:

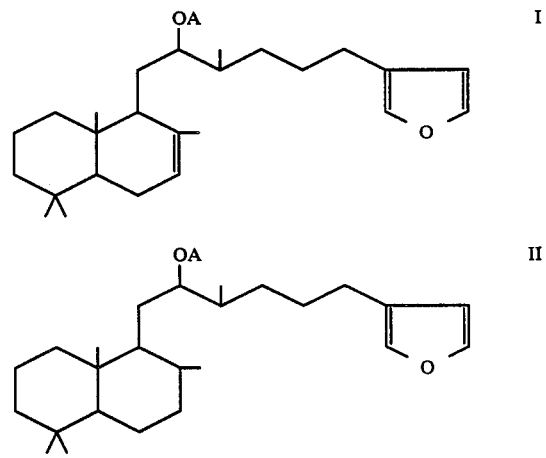

wherein:
A is $SO_3X$, R or $OCOR^1$;
R is hydrogen or $R^1$,
$R^1$ is alkyl, preferably lower alkyl,
X is H, Z or M,
M is alkali metal ion,
Z is $NH_2=C(NR_1)_2^+$ or $NHR_3^+$,
Compounds of formula II are dihydro derivatives of the compounds of formula I.
Specific examples of:
$R^1$ are C1-C5 alkyl, including methyl, ethyl, propyl, isopropyl, butyl, isobutyl, & amyl; isooctyl; hexyl; dodecyl; etc.
M are $Na^+$, $K^+$, $Li^+$.
Z are protonated counterions of ammonia, guanidine, N-methyl guanidine, N,N-dimethyl guanidine, tetramethyl guanidine, N-methyl,N'-ethyl guanidine, methyl amine, dimethyl amine, amylamine, ethyl amine, triethyl amine, methyl dipropyl amine, isooctyl amine, etc.

Preferred compounds of the invention are those of the formula III in which the substituents are as noted above:

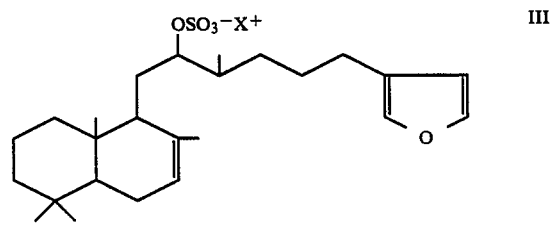

and the dihydro derivatives thereof.

In preferred embodiments of the invention, the new compounds are substantially pure.

Also provided by discoveries of the invention are pharmaceutical compositions containing between about 0.01 to 50%/w of one of the new compounds of the invention or a mixture of two or more of such compounds and one or more non-toxic, compatible ingredient, e.g., carrier, diluent and/or adjuvant.

Additionally provided by discoveries of the invention are agricultural fungicidal compositions containing between about 1 to 70%/w of one of the new compounds of the invention or a mixture of two or more of such compounds and one or more compatible ingredients, e.g., diluent, carrier, wetting agent, herbicide, adhesive agent, etc.

The invention provides a variety of processes for the production of compounds of the invention. A preferred method of producing compounds of the formula III comprises the steps of collecting marine sponge of the genus Ircinia, contacting such sponge with a selected organic solvent system to obtain an extract, fractioning the extract and isolated sesterterpene compounds of formula III from the fractionated extract.

In further preferred methods of the invention, compounds of the formula II are made by hydrogenation of the compounds I in the presence of a hydrogenation catalyst. Also, ion-exchange, hydrolysis, alkylation, acetylation and other known synthesis type reactions may be used pursuant to known procedures to add or modify various groups in the preferred compounds III to produce other compounds according to the formulae I & II.

As a result of the discoveries by the invention of the new compounds, skilled chemists will be able to use known procedures to synthesize these compounds from available stock substances.

The objects are further accomplished according to the invention by the discovery that growth of fungi can be inhibited by contact with an effective amount of the new compounds.

DESCRIPTION OF THE PREFERRED EMBODIMENTS

A more complete understanding of the invention can be obtained by reference to preferred embodiments of the invention which are illustrated by the following specific examples of compounds, compositions and methods of the invention. It will be apparent to those skilled in the art that the examples involve use of materials and reagents that are commercially available from known sources, e.g., chemical supply houses, so no details are given respecting them.

EXAMPLE 1

This example concerns the preparation of sulfircin, i.e., the compound of the formula IV:

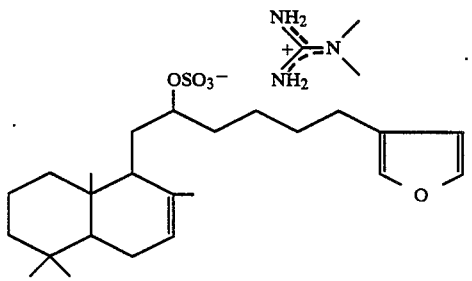

IV

Marine sponge of the genus *Ircinia aff. I. paucifilamentosa* Vacelet, 1961 was collected at a depth of 120 meters off Fresh Creek, Andros, Bahamas. *Ircinia aff. I. paucifilamentosa* Vacelet, 1961 is an amorphous to spherical sponge, grey to white alive, white in ethanol; surface conulose, with conules 2-3 mm in height and 3-4 mm apart. Choanosome is typical for the genus Ircinia. Spongin filaments are unusually thick (6 um) and terminal knobs are large and ovoid (14-16 um long). The specimens, all collected from deep water environments in the Bahamas, may be conspecific with the Mediterranean species *Ircinia paucifilamentosa* Vacelet, 1961 (Rev. Trav. Inst. Peches marit., 25(3); 351-354). Taxonomic reference samples are deposited at the Harbor Branch Oceanographic Institution/Indian River Coastal Zone Museum.

An extract of the sponge is prepared by homogenizing in a blender. The crude extract is filtered and then concentrated by distillation under reduced pressure yielding a pale yellow oil. This oil is chromatographed under reverse phase vacuum liquid chromatographic conditions using a C-18 stationary phase and a step gradient of acetonitrile/water as eluent. The fraction eluting with acetonitrile/water (4:1) contains a microcrystalline solid which is recrystallized from a dichloromethane/methanol/water mixture to give sulfircin (IV).

Using typical spectral measurement techniques and apparatus, the following spectral data are determined for sulfircin:

$^{13}$C NMR (90 Mhz, CDCl$_3$-d$_4$-methanol):

158.3 s, 142.7 d, 138.9 d, 135.8 s, 125.2 s, 122.2 d, 111.1 d, 83.9 d, 50.1 d, 48.8 d, 42.3 t, 38.7 t, 37.8q (2C), 37.0 d, 36.5 s, 33.2 q, 33.1 s, 33.1 t, 28.3 t, 26.6 t, 24.9 t, 23.9 t, 22.4 q, 21.9 q, 18.9 t, 13.6 q, 13.1 q.

$^1$H NMR (360 MHz, CDCl$_3$-d$_4$-methanol):

7.25 (t J=1.2 Hz), 7.01 (bs), 6.07 (d J=1.2 Hz), 5.18 (bs), 4.33 (dd J=11.3, 3.1 Hz), 2.844 (6H, s), 2.24 (2H, t J=7.5 Hz), 2.10 (2H, m), 2.04 (2H, m), 1.73 (2H, m), 1.60 (m), 1.51 (3H, bs), 1.50 (m), 1.42 (m), 1.33 (m), 1.22 (2H, m), 1.21 (m), 1.18 (m), 1.05 (m), 1.04 (m), 0.99 (m), 0.97 (m), 0.97 (m), 0.76 (3H, d J=7.0 Hz), 0.69 (3H, s), 0.65 (3H, s), 0.55 (3H, s).

IR: (KBr) νcm−1:

3340, 3200, 2920, 1620, 1445, 1380, 1360, 1210, 1050, 1020, 960, 900, 870, 820, 746, 775.

UV: MeOH λmax=208; (ε=1024).

MS: (FAB) M/Z=627.49 (IV +N,N-dimethylguanidine).

EXAMPLE 2

This example concerns sulfircin A, a dihydro derivative of sulfircin which is represented by the following formula:

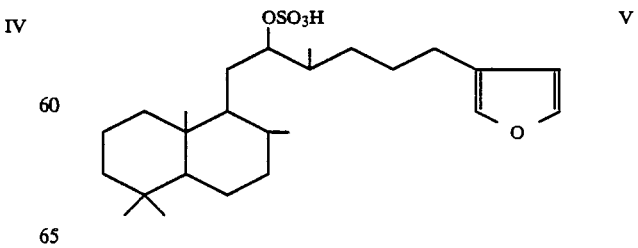

V

A portion of sulfircin and a small amount of hydrogenation catalyst, e.g., Pd/C, Pt/C or Raney Ni are mixed in a suitable solvent, e.g., ethanol or methanol. The mixture is stirred in the presence of hydrogen in a hydrogenation apparatus capable of operation at elevated pressure, e.g., Parr apparatus, to produce dihydrosulfircin. If the reaction is too slow, it is facilitated by making the media slightly acidic by addition of a trace amount of HCl or like acid.

EXAMPLE 3

This example concerns in vitro fungicidal activity of compounds of the invention against the fungal pathogen *Candida albicans*.

ASSAY METHOD

Preparation of Inocula

*C. albicans* (CA) is grown on Sabouraud dextrose agar to produce single colonies, one of which is used to inoculate Sabouraud dextrose broth. This broth is incubated at 37° C. with shaking at 200 rpm for 18 hrs., the resultant culture is frozen with 10% (v/v) glycerol at −80° C. and used as the innoculum for the anti-Candida assay.

*Aspergillus nidulans* (AN): AN (ATCC strain 36321) is grown from a spore stock on the surface of a YAG plate (YAG: Yeast extract 0.5%; glucose 2%; agar 2%) at 30° C. until the colony sporulates, at this point the colony is green (usually within one week). The spores are harvested from this plate by washing with 0.1% (v/v) Triton X-100 (filter sterilized) and spores are then washed with distilled water before freezing at −80° C. in the presence of 10% (v/v) glycerol. 1. AN Disc diffusion assay AN is inoculated into melted yeast extract glucose agar at 45° C. to give a cell density of approximately 1000 spores/ml. Plates are prepared with 10 ml of the seeded agar in a 10 cm × 10 cm petri dish. These plates are stored at 4° C. until needed for the assay.

Paper discs (6.35 mm) are impregnated with the test substance and allowed to dry. They are then placed onto the surface of the test plate prepared as detailed above. Plates are incubated overnight at 30° C. after which the zones of growth inhibition are read, being expressed as the diameter of the zone in millimeters.

2. *Candida albicans* (CA): Minimum Inhibitory Concentration (MIC)

Two-fold dilution for the test compound are prepared in 50 ul volumes of Sabouraud dextrose broth using 96-well microtiter plates. An inoculum of CA is added in a small volume to give a cell density of about 1000 cells/ml. Plates are incubated at 37° C. overnight. 10 ul of triphenyl tetrazolium chloride (1%w/v) is then added to each well and a further 2 hour incubation results in a deep coloration of the microorganism. The MIC is the lowest concentration of the test compound which completely inhibits growth of the CA.

Assay Data for Sulfircin

CA MIC 25 ug/ml.

AN Disc° diffussion assay, 12 mm zone at 25 ug/disc

EXAMPLE 4

Preparation of sulfircin B, i.e., the free acid compound:

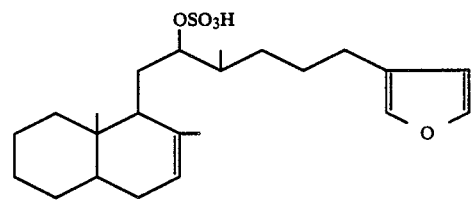

A portion of sulfircin dissolved in methanol is passed into an anion exchange column. Thereafter, the column is eluted with dilute HCl to yield sulfircin B. In related manner, sulfircin derivatives containing other counterions then N,N-dimethyl guanidine, e.g., alkali metal, ammonia, guanidines, amines, etc., can be prepared by the use of other eluents than HCl, e.g., acetic acid, formic acid, ammonium hydroxide, ammonium floroborate, dilute NaOH solution, etc.

EXAMPLE 5

Preparation of sulfircin C, the compound:

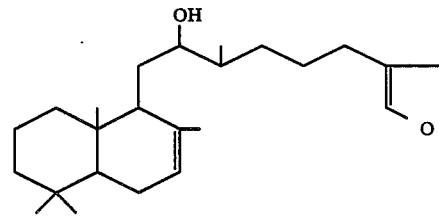

A portion of sulfircin is reacted with 25% w/w caustic soda solution and sulfircin C is recovered by extraction from the reaction mixture with chloroform. The methyl ether of sulfircin C, i.e. sulfircin D, is prepared by reaction of sulfircin C with methyl iodide in the presence of base, e.g., potassium t-butoxide.

EXAMPLE 6

Preparation of sulfircin E, the compound:

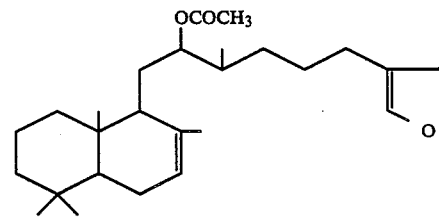

A portion of sulfircin C is reacted with a mixture of acetic anhydride and pyridine. Sulfircin E is recovered by extraction with chloroform from the reaction mixture.

Discussion of Variables

The scope of the invention is not limited by the specific examples and suggested procedures and uses related herein since modifications can be made within such scope from the general information provided by this specification to those skilled in the art. In addition to hydrogenated derivatives as exemplified above, fluorinated and salt derivatives may be prepared and have pharmaceutical activity.

Therapeutic and prophylactic application of the new compounds and compositions containing them can be contemplated to be accomplished by any suitable method and technique presently or prospectively known to those skilled in the art. Further, the compounds of the invention have use as starting materials or intermediates for the preparation of other useful compounds and compositions.

The administration of sulfircin and other compounds of the invention is useful for treating fungal infections. Thus, pharmaceutical compositions containing compounds of the invention as active ingredients are useful in prophylactic or therapeutic treatment of humans or other mammals infected with or likely to be infected with fungii.

The dosage administered will be dependent upon the identity of the fungal infection, the type of host involved, its age, health, weight, kind of concurrent treatment, if any, frequency of treatment, therapeutic ratio and like considerations. Advantageously, dosage levels of the administered active ingredients can be: dermal, 1 to about 500 mg/kg; orally, 0.01 to 200 mg/kg; intranasal 0.01 to about 100 mg/kg and aerosol 0.01 to about 50 mg/kg of animal body weight.

Expressed in terms of concentration, the active ingredient of the invention can be present in the new compositions for localized use dermally, intranasally, bronchially, intravenously, intravaginally, intramuscularly or orally in a concentration of from about 0.01 to about 50% w/w of the composition, and especially from about 0.1 to about 30% w/w of the composition.

The compositions of the invention are advantageously used in a variety of forms, e.g., tablets, ointments, capsules, pills, powders, aerosols, granules and oral solutions or suspensions and the like containing the indicated suitable quantities of the active ingredient. Such compositions are referred to herein and in the accompanying claims generically as "pharmaceutical compositions". Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such a cosolvents, wetting agents, etc.

Where the pharmaceutical compositions are ointments, the active ingredient can be mixed with a diluent vehicle such as cocoabutter, viscous polyethylene glycols, hydrogenated oils and such mixtures can be emulsified if desired.

In accordance with the invention, pharmaceutical compositions comprise, as an active ingredient, an effective amount of one or more of the new compounds and one or more non-toxic, pharmaceutically acceptable ingredient. Examples of such ingredients for use in the compositions include, ethanol, dimethyl sulfoxide, glycerol, silica, alumina, starch, calcium carbonate, talc, flour, and equivalent non-toxic carriers and diluents.

In preferred embodiments for production of the new compounds by extraction from marine sponges, etc., suitable organic solvent systems for extraction can be selected from methanol, ethyl acetate, acetone, diethyl ether, t-butyl methyl ether, ethanol, and isopropanol. Mixtures of two or more of such solvents in various ratios and combinations are advantageous.

Compounds of the invention are synthesized and/or isolated by various fractionation and chromatographic techniques from the extracts obtained as disclosed. Preferred isolation procedures include various chromatography techniques, e.g., countercurrent chromatography with suitable columns, including multi-layer planetary coil columns. A variety of solvents are available for use as single or mixed eluents, such as tetrahydrofuran, methanol, ethyl acetate, acetonitrile, n-propanol, n-butanol, water, and equivalent solvents. Further purifications using such procedures may also be carried out on the recovered extractions. Preferred isolation techniques for further purification include chromatographic operations such as high-pressure, liquid chromatography with suitable columns and suitable solvents.

THE EMBODIMENTS OF THE INVENTION IN WHICH AN EXCLUSIVE PROPERTY OR PRIVILEGE IS CLAIMED ARE DEFINED AS FOLLOWS:

1. A compound selected from the formulae I & II:

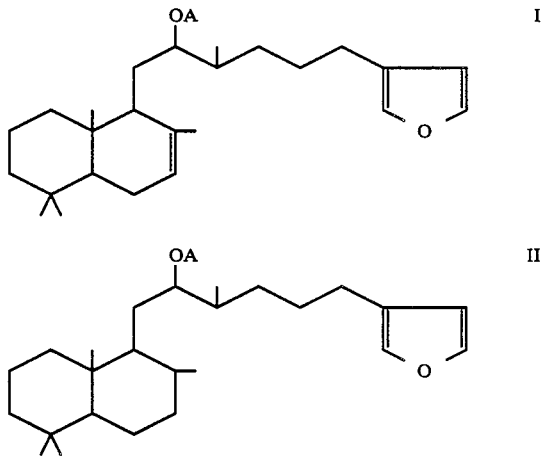

wherein:
A is $SO_3X$, R or $OCOR^1$;
R is hydrogen or $R^1$,
$R^1$ is alkyl,
X is H, Z or M,
M is alkali metal ion,
Z is $NH_2=C(NR_2)_2$ or $NHR_3$ ion.

2. A compound of the formula:

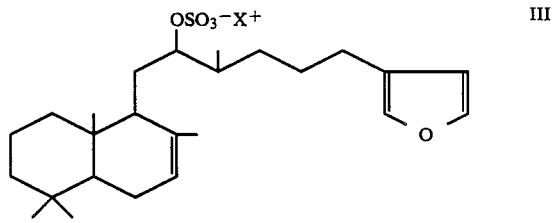

wherein:
X is H, Z or M,
M is alkali metal ion,
Z is $NH_2=C(NR_2)_2$ or $NHR_3$ ion.

3. The compound of claim 2 wherein X is the N,N-dimethyl guanidinium counterion.

4. The compound of claim 1, formula I, wherein A is R.

5. A pharmaceutical composition comprising between about 0.01 to 50% by weight based on the total weight of said composition as an active ingredient one or more compounds of claim 1 and a non-toxic carrier or diluent.

6. A pharmaceutical composition comprising between about 0.1 to 25% by weight based on the total weight of said composition as an active ingredient one or more compounds of claim 2 and a non-toxic carrier or diluent.

7. A pharmaceutical composition comprising between about 0.1 to 25% by weight based on the total weight of said composition as an active ingredient the compound of claim 3 and a non-toxic carrier or diluent.

* * * * *